United States Patent [19]
Burke

[11] Patent Number: 5,330,757
[45] Date of Patent: Jul. 19, 1994

[54] METHOD FOR THE PREVENTION AND REVERSAL OF THE EXTRINSIC AGING OF THE SKIN BY TRANSDERMAL APPLICATION OF SELENAMINO ACIDS AND COMPOSITIONS THEREFORE

[76] Inventor: Karen E. Burke, 420 E. 51st, New York, N.Y. 10022

[21] Appl. No.: 147,902

[22] Filed: Nov. 4, 1993

Related U.S. Application Data

[63] Continuation of Ser. No. 886,501, May 20, 1992, abandoned.

[51] Int. Cl.$^5$ .............................................. A61K 13/00
[52] U.S. Cl. ...................................... 424/449; 424/424
[58] Field of Search ................................ 424/449, 424

[56] References Cited

U.S. PATENT DOCUMENTS

| | | | |
|---|---|---|---|
| 4,727,088 | 2/1988 | Scott et al. | 514/859 |
| 4,865,840 | 9/1989 | Burke | 514/937 |

*Primary Examiner*—Paul R. Michl
*Assistant Examiner*—William E. Benston, Jr.

[57] ABSTRACT

Provided is a method for enhancing and accelerating the repair of chronic cellular and molecular damage to skin. Also provided is a method for thinning stratum corneum of mammalian, preferably human, skin thickened by extrinsic free radicals and restoring elastic tissue damaged by extrinsic free radicals. Both methods comprise the topical administration to mammalian, preferably human, skin of a composition comprising selenoamino acids in a pharmaceutically acceptable transdermal carrier.

18 Claims, No Drawings

METHOD FOR THE PREVENTION AND REVERSAL OF THE EXTRINSIC AGING OF THE SKIN BY TRANSDERMAL APPLICATION OF SELENAMINO ACIDS AND COMPOSITIONS THEREFORE

This is a continuation of copending application Ser. No. 07/886,501 filed on May 20, 1992, now abandoned.

BACKGROUND OF THE INVENTION

1- Field of the Invention

This invention relates to a method for enhancing and accelerating the repair of chronic cellular and molecular damage to the skin.

2- Description of the Prior Art

Recently it has become apparent that chronic free radical damage to the skin either from UV irradiation or from environmental pollutants causes specific deterioration of the epidermis and dermis that is distinct from the acute effects of UV irradiation and is not simply an acceleration of the inevitable age-dependent alterations denoted in the dermatologic literature as "intrinsic" aging.

The particular chronic cumulative damage caused by UV irradiation is denoted in the medical dermatologic literature as "photoaging" and is manifested clinically by wrinkles, dry, waxy skin, and a variety of benign and premalignant as well as malignant neoplasms. All of these clinical changes are the result of specific salient histologic features of actinically damaged skin which have been characterized and are (i) hypertrophy of the epidermis with cellular atypia and thickening of the stratum corneum, (ii) solar elastosis with tangled, degraded dermal elastic tissue degeneration into an amorphous mass (Kligman AM, JAMA, 210, 2377, 1969), (iii) degradation of dermal collagen to become larger rope-like structures (Bentley JP, J. Invest. Dermatol. 73, 80, 1979), and (iv) hypercellularity of the dermis (Andrew W, et al: Gerontologica 10, 1, 1964).

Topical application of retinoic acid (Retin A, Ortho Pharmaceutical Corporation) reportedly results in epidermal repair with thinning of the excessive stratum corneum and normalization of the cellular atypia of the deeper layers of the epidermis as well as the formation of new, fine fibrillar dermal collagen and restructuring of the damaged dermal elastic tissue to the normal non-tangled, fibrillar form. (Kligman AM, Leyden JJ, Kligman LH, Grove GL, Topical Retinoic Acid for the reversal of Photoaging, Communication from Ortho Pharmaceutical Corporation, February 1986; Weiss JS. Ellis CN, Headington JT, Tincoff T, Hamilton TA, Voorhees JJ, JAMA 259, 527, 1988). However, the use of topical retinoic acid usually causes discomfort, flaking and erythema at the beginning of treatment and increased sensitivity to sunlight (Burke KE, Graham GF, North Carolina, New York, JAMA 260, 3130, 1988).

It has previously been shown that topical application of selenamino acids leads to transdermal absorption with enhanced levels of selenium in the skin to provide protection from UV irradiation induced skin damage, significantly reducing the incidence of skin cancers following UV light exposure (U.S. Pat. No. 4,865,840 Sep. 12, 1989). The levels of selenium that were effective gave no evidence of any topical or systemic toxicity.

A need exists for additional methods for enhancing and accelerating the repair of chronic cellular and molecular damage to skin, especially methods not having the side effects of topically applied Vitamin A.

SUMMARY OF THE INVENTION

In one embodiment, the present invention provides a method for enhancing and accelerating the repair of chronic cellular and molecular damage to skin. The method comprises the topical administration to mammalian, preferably human, skin of a composition comprising selenoamino acids in a pharmaceutically acceptable transdermal carrier.

In another embodiment, the invention provides a method for thinning the stratum corneum of mammalian, preferably human, skin thickened by extrinsic free radicals and restoring elastic tissue damaged by extrinsic free radicals. The method comprises the topical administration to the skin of a composition comprising selenoamino acids in a pharmaceutically acceptable transdermal carrier.

DETAILED DISCUSSION

The present invention relates to the reversal of extrinsic chronic damage to the skin induced by the generation of free radicals by environmental factors including, but not limited to, ultraviolet (UV) irradiation and environmental pollutants, by the topical, transdermal application of selenoamino acids, preferably the application is continuous and, more preferably, long term.

The terms "topical, transdermal" "topical" or "transdermal" used herein, indicate that the composition is topically applied and transdermally absorbed.

Recently the distinction between extrinsic and intrinsic aging of the skin has been clarified on an histologic level. Extrinsic aging is due to environmental insults, particularly those which generate free radicals, such as, UV irradiation and pollutants, i.e., cigarette smoke, while intrinsic aging occurs naturally with the passing of time. The chronic clinical and histological manifestations of extrinsic aging are also quite distinct from the acute insult of sunburn.

Transdermal application of compositions containing selenoamino acids has been found to accelerate and enhance the repair of the chronic damage done to both the epidermal and dermal layers of the skin by these extrinsic environmental insults—even when applied after the damage had already occurred. This reversal of chronic damage is of utmost importance because if untreated, these environmental insults lead to not only the appearance of premature aging, but also to an observed increase in precancerous lesions as well as to skin cancer.

Natural repair of the above chronic damage with cellular repair of the epidermis and molecular repair of the dermal collagen and elastic tissue is not as rapid and takes far longer than repair with the transdermal treatment described herein using a composition comprised of topical selenoamino acids and optionally containing other active cellular protective and repairing compounds, including, carotenes, retinoids, e.g., retinoic acid, and isomers of tocopherol and the ester derivatives.

As noted above, the side effects of topical retinoic acid compositions of the prior art used for reversing the effects of photoaging usually causes discomfort, flaking and erythema at the beginning of treatment and increased sensitivity to sunlight. Such adverse effects are not noted with topical, transdermal application of selenoamino acids, in fact, the such applications of selenoamino acids actually decreases sensitivity to sunlight. Furthermore, the topical, transdermal, selenoamino acids are even more effective and act more rapidly in reversing the cellular and molecular damage to photoaged skin than does topical retinoic acid.

The inventor has found that the long-term transdermal application of selenoamino acids reverses the effects of photoaging clinically and histologically. In particular, topical application of selenoamino acids results in transdermal absorption to cause epidermal repair with thinning of the excessive stratum corneum and normalization of the cellular atypia of the deeper layers of the epidermis as well as the formation of new, fine fibrillar dermal collagen and restructuring of the damaged dermal elastic tissue to the normal non-tangled, fibrillar form.

From the state of the art, the new and novel method of long-term topical, continued transdermal application of selenoamino acids to reverse previously acquired free radical damage to the skin (especially from UV irradiation but also from other sources such as environmental pollutants including cigarette smoke) was neither obvious nor foreseeable.

Selenoamino acid compositions used in the methods of the present invention can be provided in any suitable carrier. For example, suitable carriers are those which actually penetrate the skin and include oil-in-water emulsions of polypropylene glycol-3-myristyl ether, squalane, other unsaturated oils and branched hydrocarbons, liquid fatty acid esters, unsaturated liquid fatty alcohols and unsaturated vegetable oils formulated as hydrophilic lotions or creams. Thus the carrier may also include humectants such as glycerine or propylene glycol and other conventional additives. For example, known oil-in-water emulsions used as face or hand skin bases may be advantageously employed. Preferably, the transdermal carrier provides transdermal transport of the selenoamino acids to cells, molecules or matrix components of the skin damaged by environmental factors.

According to the present invention, selenoamino acids, preferably L-selenomethionine, can be incorporated into, for example, a lotion or cream-type transdermal carrier at a concentration by weight or at least 0.002%, preferably 0.02% to 0.5%, more preferably about 0.05% to produce a composition applicable to the skin.

To obtain optimal effect, the composition should be applied multiple times per week on different days continually, i.e., for the length of time that the therapeutic effect is desired. Although corrective effects can be demonstrated with two months in humans, in order to reverse optimally the previously incurred extrinsic damage to the skin, application should be multiple, preferably at least five, times per week on different days for at least nine months.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example; unless otherwise indicated, all parts and percentages are by weight.

EXAMPLE

It was of interest to ascertain whether topical selenoamino acid, in particular, L-selenomethionine, could not only partially prevent or inhibit both acute and chronic UV-induced damage to the skin by decreasing the blistering of sunburn and the pigmentation and by retarding the onset and decreasing the incidence of skin cancers as has been shown previously (U.S. Pat. No. 4,865,840, Sep. 12, 1989), but also partially reverse the long-term alterations in the epidermis denoted as "photoaging."

Twenty-four Skh:2 hairless, pigmented, dark-eyed female mice were separated into groups as shown in Table 1.

TABLE 1

REVERSAL OF PHOTOAGING
EXPERIMENTAL TREATMENT GROUPS

| GROUP | # MICE | UV | TREATMENT |
|-------|--------|----|-----------|
| 1a | 6 | + | Vehicle |
| 1b | 2 | − | Vehicle |
| 2a | 6 | + | Topical Retinoic Acid 0.05% |
| 2b | 2 | − | Topical Retinoic Acid 0.05% |
| 3a | 6 | + | Topical L-Selenomethionine 0.05% |
| 3b | 2 | − | Topical L-Selenomethionine 0.05% |

Since topical retinoic acid cream 0.05% (Retin A, Ortho Pharmaceutical Corp.) is the only medication which has been shown to reverse partially the structural abnormalities in photoaged skin, this treatment was included in the experiment as a control to demonstrate the optimal known reversal of the cellular and molecular changes designated in the medical dermatologic literature as extrinsic aging or photoaging (Communication from Ortho Pharmaceutical Corp., February 1986; Weiss JS, Ellis CN, Headington JT, Tincoff T, Hamilton TA, Voorhees JJ, JAMA 259, 527, 1988).

Twenty-four mice were exposed to UV irradiation with four Westinghouse FS40 sunlamps beginning at 2.5 minute exposures and increased by 2.5 minutes (about 0.24 Joules/sq.cm./exposure). The irradiation was given five days per week for twelve weeks (about 10 Joules/sq.cm./exposure). Irradiation has been shown to induce the structural abnormalities of photoaged skin in this breed of mice.

After termination of the UV irradiation, the irradiated mice were divided into the treatment groups, 1a, 2a, and 3a, so that each group had a similar distribution of relatively darker and relatively lighter pigmented mice (since clinically the degree of hyperpigmentation in each mouse is slightly different); the control "b" groups (treated with vehicle alone) each had one dark and one medium dark brown mouse. Individual mice were identified by clipping the ears. To the back of each mouse 0.1 ml of each composition listed in Table 1 was applied daily five days per week for ten weeks. Duplicate punch biopsies were taken from the mid-backs of each mouse prior to application of the creams and after five and ten weeks for histologic analysis in order to evaluate the effectiveness of topical L-selenomethionine in comparison with retinoic acid in partially reversing the UV-induced photoaging of the epidermis and dermis.

Table 2 demonstrates that topical L-selenomethionine is effective in reversing the structural abnormalities of photoaged skin. In fact, topical L-selenomethionine is more effective than topical retinoic acid under the study conditions. No histologic changes were detected in any of the mice not exposed to UV, even with the applications of the compositions.

TABLE 2
REVERSAL OF PHOTOAGING WITH TOPICAL L-SELENOMETHIONINE

|  | Veh | Veh# | Veh* | RA* | SeMet* |
|---|---|---|---|---|---|
| Prior UV irradiation | — | + | + | + | + |
| Epidermal thickness (mm) | 0.02 | 0.16 | 0.12 | 0.09 | 0.07 |
| Hyperkeratosis of stratum corneum | 0 | 3 | 3 | 2 | 0.5 |
| Solar elastosis | 0 | 3 | 3 | 1 | 1 |
| Collagen disruption | 0 | 3 | 3 | 1 | 1 |
| Net Graduation | 0 | 9 | 9 | 4 | 2.5 |

Veh = Vehicle
RA = retinoic acid (0.05%)
SeMet = L-Selenomethionine (0.05%)
\# = Immediately after UV irradiation
* = After ten weeks' treatment
Gradation: 0 = minimal, 3 = maximal As has been documented in the scientific literature cited above and can be noted in Table 2, UV irradiation causes hyperplasia of the epidermis with cellular atypia and marked hyperkeratosis of the stratum corneum (so that the epidermis in the Skh:2 mice became 0.16 mm in depth compared with depth of 0.02 mm in non-UV-irradiated mice). The other histologic features which characterize free radical damaged skin are graded in Table 2. The most prominent feature of the damage to the dermis is the so-called "solar elastosis"—marked degeneration of the elastic tissue with the normally sparse, delicate fibers replaced by degraded, thickened, twisted fibers. Also, there is disruption of the collagen with the normally fine, fibrillar collagen replaced by clumped, irregular bundles, dispersed in disarray. The dermis is hypercellular with many inflammatory cells, particularly mast cells. Natural repair of this chronic damage or attempted repair by topical application of vehicle alone results in only very minimal reversal of the cellular and molecular manifestations of photoaging in the time span studied (up to fifteen weeks).

As shown in Table 2, application of the vehicle alone for ten weeks reduces the hyperplasia of the epidermis only slightly with little resolution of the cellular atypia and only minimal thinning of the reactive hyperkeratosis of the stratum corneum (such that the epidermal thickness is decreased from 0.16 mm to 0.12 mm). There is little repair of the degraded collagen or elastic tissue: Still after ten weeks (and even after fifteen weeks, not cited in Table 2) the elastic fibers are thickened, twisted, and clumped into amorphous masses indicative of solar elastosis and the collagen fibers are irregularly thickened and dispersed in disarray. There is still marked hypercellularity in the dermis with many mast cells.

Topical application of retinoic acid and of L-selenomethionine repairs all manifestations of this cellular and molecular damage. Topical application of retinoic acid reduces the epidermal hyperplasia, decreases the degree of cellular atypia, and decreases the hyperkeratosis of the stratum corneum, reducing the epidermal thickness from 0.16 mm to 0.09 mm after ten weeks.

Topical application of L-selenomethionine is even somewhat better than topical retinoic acid at repairing the epidermal cellular damage of UV irradiation: the epidermal hyperplasia is reduced, cellular atypia decreased, and the hyperkeratosis of the stratum corneum decreased, so that the epidermal thickness is equal to 0.07 mm after ten weeks.

The topical L-selenomethionine composition is also more effective than topical retinoic acid in repairing the damaged dermis. After treatment for ten weeks with topical retinoic acid, there is some repair of the dermis: a distinct repair zone is noted in the upper dermis with many fibroblasts and some replacement of the clumped, irregular collagen bundles with normal, fine, fibrillar collagen. After treatment for ten weeks with L-selenomethionine, almost the whole dermis contains fibroblasts and shows repair of the previously degraded collagen to form fine, fibrillar collagen arranged with the regular fibers parallel to the surface of the skin as in non-UV-irradiated skin. After treatment with topical retinoic acid for 10 weeks, there is only minimal repair of the solar elastosis, so that normal, delicate elastic fibers are noted throughout the dermis with no amorphous masses of degraded elastic tissue.

Therefore after subjective evaluation of the parameters of damage to the epidermis and dermis induced by UV irradiation, the repair is more effectively and more rapidly accomplished with topical L-selenomethionine than with topical retinoic acid.

The preceding example can be repeated with similar success by substituting the generically described reactants of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for enhancing and accelerating the repair of chromic cellular and molecular damage to mammalian skin, the method comprising topical administration to skin requiring such repair of a composition consisting essentially of selenoamino acids in pharmaceutically acceptable transdermal carrier, wherein the selenoamino acids are present at a concentration by weight of at least about 0.05% based on the total weight of the composition.

2. The method of claim 1, wherein the selenoamino acid is L-selenomethionine.

3. The method of claim 1, wherein the concentration of selenomethionine is about 0.05% to 0.5% by weight.

4. The method of claim 1, wherein the concentration of the selenomethionine is about 0.5% by weight.

5. The method of claim 1, wherein the composition is administered at least five times a week for at least two months.

6. The method of claim 1, wherein the damage is produced by environmental factors.

7. The method of claim 1, wherein the environmental factors are ultraviolet irradiation and environmental pollutants.

8. The method of claim 1, wherein the damage results in photoaging.

9. The method of claim 1, wherein the transdermal carrier provides transdermal transport of the selenoamino acids to cells, molecules or matrix components of the skin damaged by environmental factors.

10. The method of claim 1, wherein the composition further comprises a carotene, a retinoid or an isomer of tocopherol or its ester derivatives.

11. A method for thinning stratum corneum of mammalian skin thickened by extrinsic free radicals and restoring elastic tissue damaged by extrinsic free radicals, the method comprising topical administration to mammalian skin requiring such thinning and restoring of a composition consisting essentially of selenoamino acids in a pharmaceutically acceptable transdermal carrier, wherein the selenoamino acids is present at a concentration by weigh of at least about 0.05% based on the total weight of the composition.

12. The method of claim 11, wherein the selenoamino acid is L-selenomethionine.

13. The method of claim 11, whether the concentration of selenomethionine is about 0.05% to 0.5% by weight.

14. The method of claim 11, wherein the concentration of the selenomethionine is about 0.5% by weight.

15. The method of claim 11, wherein the composition is administered at least five times a week for at least two months.

16. The method of claim 11, wherein the composition further comprises a carotene, a retinoid or an isomer of tocopherol or its ester derivatives.

17. The method of claim 1, wherein the concentration of the selenomethionine is about 0.05% by weight.

18. The method of claim 11, wherein the concentration of the selenomethionine is about 0.05% by weight.

* * * * *